(12) United States Patent
Giuliani et al.

(10) Patent No.: US 11,376,211 B2
(45) Date of Patent: Jul. 5, 2022

(54) COMPOSITION FOR THE PREVENTION AND TREATMENT OF SKIN DAMAGES CAUSED BY PHOTO-EXPOSURE

(71) Applicant: GIULIANI S.P.A., Milan (IT)

(72) Inventors: Giammaria Giuliani, Montagnola (CH); Fabio Rinaldi, Milan (IT); Walter Bertin, Istrana (IT); Marzia Pellizzato, Fanzolo di Vedelago (IT); Barbara Marzani, Carbonara Al Ticino (IT); Daniela Pinto, Milan (IT)

(73) Assignee: GUILIANI S.P.A., Milan (IT)

( * ) Notice: Subject to any disclaimer, the term of this patent is extended or adjusted under 35 U.S.C. 154(b) by 49 days.

(21) Appl. No.: 16/977,557

(22) PCT Filed: Mar. 1, 2019

(86) PCT No.: PCT/IB2019/051659
§ 371 (c)(1),
(2) Date: Sep. 2, 2020

(87) PCT Pub. No.: WO2019/167010
PCT Pub. Date: Sep. 6, 2019

(65) Prior Publication Data
US 2021/0000735 A1 Jan. 7, 2021

(30) Foreign Application Priority Data

Mar. 2, 2018 (IT) .................. 102018000003232

(51) Int. Cl.
*A61K 8/9789* (2017.01)
*A61Q 17/04* (2006.01)

(52) U.S. Cl.
CPC ............ *A61K 8/9789* (2017.08); *A61Q 17/04* (2013.01)

(58) Field of Classification Search
None
See application file for complete search history.

(56) References Cited

U.S. PATENT DOCUMENTS 10,946,075 B1 * 3/2021 Paxton-Pierson ...... A61K 33/10
2014/0113031 A1 4/2014 Lee

FOREIGN PATENT DOCUMENTS

CN 106361599 A 2/2017
DE 202017002770 U1 6/2017

OTHER PUBLICATIONS

International Search Report and Written Opinion for corresponding international application PCT/IB2019/051659, dated Jun. 21, 2019.
Ali et al., "Enhancement of Human Skin Facial Revitalization by Moringa Leaf Extract Cream," Postep Derm Alergol, 2, 71-76 (2014).
Qi et al., "Lycium barbarum Polysaccharides Protect Human Lens Epithelial Cells against Oxidative Stress-Induced Apoptosis and Senescence," PLOS One, 9(10):e110275 (2014).
Gothai et al., "Chemical Composition of Moringa oleifera Ethyl Acetate Fraction and its Biological Activity in Diabetic Human Dermal Fibroblasts," Pharmacognosy Magazine 13(51): 462-469 (2017).
Li et al., "Lycium barbarum Polysaccharide Protects Human Keratinocytes Against UVB-induced Photo-damage," Free Radical Research, 51(2): 200-210 (2017).

* cited by examiner

*Primary Examiner* — Nannette Holloman
(74) *Attorney, Agent, or Firm* — Troutman Pepper Hamilton Sanders LLP (Rochester)

(57) ABSTRACT

The present invention concerns a composition comprising a *Lycium barbarum* extract or *Lycium barbarum* polysaccharide in combination with a *Moringa oleifera* extract and a pharmaceutically acceptable carrier. The composition finds application both in the medical field, in the treatment of actinic lesions, precancerous skin lesions, or non-melanoma skin cancer, and in non-therapeutic applications in the treatment of skin damage caused by exposure to the sun's rays, such as photoaging.

13 Claims, 2 Drawing Sheets

COMPOSITION FOR THE PREVENTION AND TREATMENT OF SKIN DAMAGES CAUSED BY PHOTO-EXPOSURE

This application is a national stage application under 35 U.S.C. § 371 of PCT Application No. PCT/IB2019/051659, filed Mar. 1, 2019, which claims the priority benefit of Italy Patent Application No. 102018000003232, filed Mar. 2, 2018, which are hereby incorporated by reference in their entirety.

FIELD OF THE INVENTION

The present invention relates to a composition for the prevention and treatment of skin damages caused by ultraviolet radiation exposure The present invention originates in the pharmaceutical, nutraceutical, dermatological, and cosmetic fields.

In particular, the present invention relates to a composition for preventing or treating aging from exposure to sunlight or certain skin affections caused by exposure to ultraviolet radiation, in particular the sun's rays.

STATE OF THE ART

With aging of the human body, the epidermis cells progressively lose their proliferation capacity resulting in a thinning of the skin. At the same time, in senescent skin the keratin lamellae form a compact layer causing the loss of youthful elasticity, while the slowing down of cell reproduction leads to an imbalance in the physiological process of water evaporation, and a decrease in collagen content. These phenomena linked to the physiological aging of the body can be exacerbated in subjects who have repeatedly exposed, and for prolonged periods of time, themselves to the sun's rays, especially in the absence of adequate sun protection.

In these cases, we speak of photoaging of the skin, a condition in which the physiological appearance of wrinkles and the loss of skin elasticity typical of individual mature age are accompanied by atrophy, solar elastosis, actinic purpura, and possibly even precancerous lesions, tumours, and melanoma (Pandel et al. 2013).

As regards exposure to the sun's rays, it was found that exposure to UVB rays mainly causes damage to the most superficial layers of the skin. A typical example of this damage, also associated with burning, occurs in cases of sunburn. On the other hand, UVA rays have a greater ability to penetrate the skin layers and exposure to them can lead to premature aging of the skin and appearance of actinic or precancerous lesions.

Numerous studies have also shown how exposure of the skin to UV radiation, in the absence of sunscreens, results in the formation of highly toxic products, such as free radicals, accelerates skin aging, and causes a reduction in the functionality of the epidermal stem cells themselves.

The presence of excess free radicals can also cause severe damage to nuclear and mitochondrial DNA, cell membranes, lipids, and to the proteins of skin stem cells and their progeny. In these conditions, the self-regenerative capacity of epidermal structures is compromised, with consequent acceleration of skin aging.

It has also been shown that the mechanisms of photoaging and carcinogenesis of the skin are the direct result of solar radiation effect. UV rays are, in fact, able to generate reactive oxygen species (ROSs), and thus alter cellular homeostasis.

These effects, in turn, alter the signal transduction pathways and the inflammatory cascade, and induce the extracellular matrix (ECM) remodelling which contributes to loss of skin elasticity.

It is now widely recognized that exposure to UV radiation is the main cause of oxidative stress in the skin, and one of the main causes of aging due to sun exposure.

In fact, oxidative stress is a consequence of an imbalance between ROSs production and their neutralization by cellular antioxidant systems. Non-neutralized ROSs promote different types of cell damage: lipoperoxidation to the detriment of cell membranes, alteration of structure and functionality of many enzymes, and promote carbohydrate oxidation.

In response to ROSs attacks, the skin has a protective system consisting of endogenous enzymatic and non-enzymatic antioxidants. However, the skin antioxidant system becomes less efficient during aging, and in any case is not able to buffer the continuous or excessive attacks from external agents, first of all the exposure to sun rays, to which it is subjected.

In an attempt to remedy these phenomena, preparations containing antioxidant actions have been formulated, in order to counteract the damage induced by ROSs. Some of these preparations contain antioxidant substances of vegetal origin, possessing also anti-inflammatory and immunomodulatory activity.

For example, the use of epigallocatechin-gallate and curcumin in the formulation of preparations to prevent or treat UV-induced skin damage is well known. However, recent studies have shown that the use of these substances of vegetal origin is not free from presenting side effects, such as the appearance of contact allergy to curcumin (Chaudhari et al, J Clin Aesthet Dermatol, 2015) or abdominal pain and nausea found with use of epigallocatechin-gallate (Chow et al.; Clin Cancer Res. 2003).

Therefore, there is currently a need to have preparations that prevent or reduce both the aesthetic damage to the skin, and the health risks caused by excessive or prolonged exposure to sunlight.

One of the objects of the invention is, therefore, to provide a composition based on active substances of vegetal origin suitable for preventing or treating skin damage caused by excessive or prolonged exposure to ultraviolet rays, whose use is almost devoid of side effects.

Another object of the invention is to provide a composition for the treatment and reduction of risks of developing actinic damage, precancerous lesions, or non-melanoma skin cancer resulting from prolonged or excessive exposure to sun rays.

SUMMARY OF THE INVENTION

In the technical field of the invention, the Applicant has found that by combining one or more components of a *Lycium barbarum* extract with components from a *Moringa oleifera* extract, a synergistic cellular antioxidant effect which reduces cellular oxidative stress is obtained.

Furthermore, the inventors have observed that the combination of the biologically active components present or extracted from *Lycium barbarum* and *Moringa oleifera* exert a protective and recovery action from the oxidative stress induced on human keratinocyte cell lines.

In view of the objects set forth above, the present invention provides, in accordance with a first aspect, a composition comprising a *Lycium barbarum* extract or *Lycium barbarum* polysaccharide in combination with a *Moringa*

*oleifera* extract, for use in the prevention or treatment of skin lesions caused by exposure to ultraviolet radiation, such as actinic damage and/or lesions, precancerous skin damage and/or lesions, or non-melanoma skin cancer (NMSC).

Typically, the aforementioned skin lesions and/or NMSC forms originate or are formed following exposure of the skin to ultraviolet rays, particularly to the sun's rays.

Within the scope of application in the medical field, the composition of the invention is particularly indicated in the treatment of actinic damage, precancerous lesions or non-melanoma cancer, i.e. cancer other than melanoma, of the skin following prolonged or excessive exposure to the sun's rays.

According to a second aspect, the invention provides the non-therapeutic use of a *Lycium barbarum* extract or polysaccharide LBP in combination with a *Moringa oleifera* extract to prevent or treat a skin aesthetic damage, or skin aging and/or the inherent signs caused by exposure to ultraviolet radiation, in particular the sun's rays.

In accordance with this aspect, the composition of the invention finds a cosmetic application in preventing or treating skin damage caused by prolonged exposure to the sun's rays which cause premature skin aging.

Typically, the composition of the invention is indicated in the non-therapeutic/cosmetic field in preventing and/or treating premature skin aging, photoaging, in particular due to oxidative stress resulting from exposure to ultraviolet rays.

BRIEF DESCRIPTION OF THE DRAWINGS

The features and advantages of the present invention will result more apparent from the enclosed drawings, wherein.

DETAILED DESCRIPTION OF THE INVENTION

Figure 1:
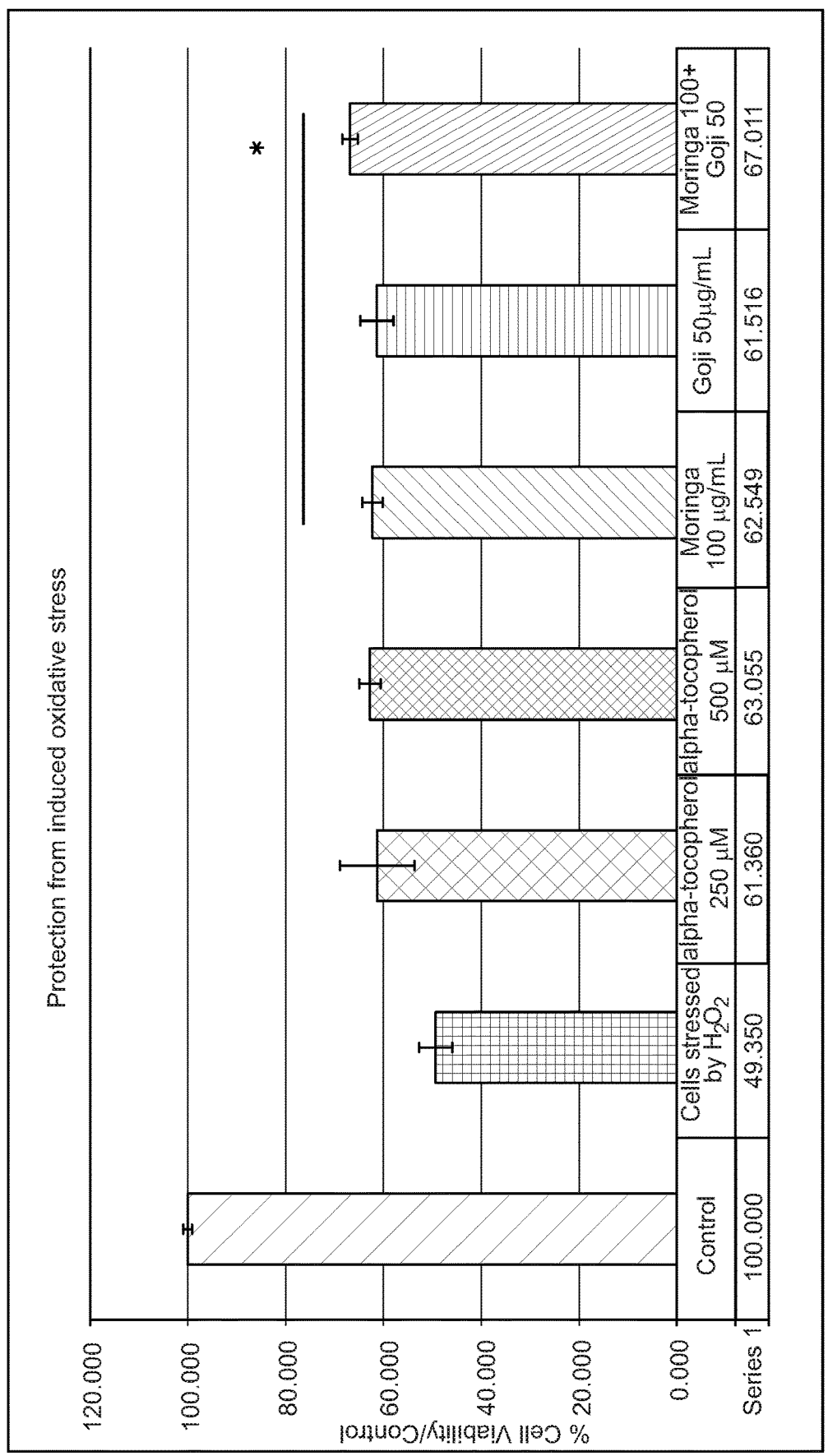
FIG. 1 illustrates bar graphs relating to cell viability percentage in human keratinocytes NCTC2544, following oxidative stress induction with 1 mM $H_2O_2$, according to the test in Example 6 on protection against induced oxidative stress.

The present invention originates from the finding that by combining a phytoextract of *Lycium barbarum* or LBP with a phytoextract of *Moringa oleifera*, a synergistic action of protection and recovery from oxidative stress in epidermal keratinocyte lines is obtained. This action allows both to prevent/treat skin cosmetic damage and prevent/treat skin lesions or damage of an actinic nature resulting from exposure to ultraviolet radiation.

In accordance with a first aspect of the invention, a composition is thus provided for use in the medical field in the treatment of skin diseases caused by exposure to ultraviolet radiation in accordance with the appended claim 1.

According to certain aspects, the invention relates to the use of the composition containing a synergistic combination of *Lycium barbarum* and *Moringa oleifera* for the treatment of subclinical conditions or diseases of the skin caused by exposure to ultraviolet radiation, typically exposure to the sun's rays.

Embodiments of the uses in the medical field of the composition of the invention are defined in the attached dependent claims 2-9.

In accordance with the first aspect of the invention, the composition based on phytoextracts has a therapeutic indication in preventing or treating skin affections caused, that originate, or that are triggered by exposure to ultraviolet radiation, in particular dermatological affections selected from actinic lesions, precancerous skin lesions, or non-melanoma skin cancer.

According to some aspects of the invention, the composition of the invention according to any one of the embodiments described herein is provided to reduce the risk of developing actinic keratosis lesions or precancerous lesions of the skin. According to these aspects of the invention, it is possible to treat a subpopulation of subjects/patients that already had these lesions in the past, with the aim of preventing their recurrence or reducing the number of relapses.

According to other aspects, the invention provides a composition containing phytocomplexes as described herein to reduce the risks and/or prevent the development of non-melanoma skin cancer, a condition defined in the literature as NMSC.

In accordance with other aspects, the invention also relates to the non-therapeutic/cosmetic use of a composition containing the combination of phytoextracts described herein in the treatment of aesthetic skin damage or skin aging caused by exposure to ultraviolet radiation.

It was observed that the composition described herein exerts a high protective and/or preventive effect on aesthetic skin damage and/or skin aging caused by photo-exposure to UVA, UVB and UVC radiations. Consequently, in one aspect the cosmetic use of a composition is provided comprising a *Lycium barbarum* extract or *Lycium barbarum* polysaccharide in combination with a *Moringa oleifera* extract and a cosmetically/physiologically acceptable carrier in the prevention or treatment of photoaging.

It was also observed that the synergism of the two components is particularly high in case of *Moringa oleifera*/*Lycium barbarum* ratios of 1:7 to 5:1, preferably 1:3 to 3:1.

One embodiment of the composition provides that *Moringa oleifera* and *Lycium barbarum* are present in a quantitative ratio of 2:1.

The synergy of action is evidenced by the experimental data illustrated in the following Example 7.

In accordance with these aspects, the composition of the invention finds application in the cosmetic treatment of skin aging signs resulting from exposure to ultraviolet radiation, typically to the sun's rays.

Typically, the composition of the invention is used in the prevention or non-therapeutic treatment of skin aging due to exposure to the sun's rays.

Furthermore, the composition of the invention may be used in preventing or treating those signs of skin aging which are attributable to repeated exposure to ultraviolet radiation over time, such as skin corrugations, skin roughness, skin thickening, dehydration, and skin wrinkling in the body and in particular in the face.

Typically, the composition of the invention may be used, both for medical and non-therapeutic applications, in the treatment of damaged skin due to exposure to UVA, UVB or UVC rays.

Typically, UV-A radiation refers to radiations with a wavelength of 315 to 400 nm; UV-B radiation refers to radiations with a wavelength of 280 to 314 nm; UV-C radiation refers to radiations with a wavelength of 100 to 279 nm.

The biologically active components present in the composition are the same for both medical and non-therapeutic use. These components, and other aspects of the composition of the invention are described in detail below.

In the composition of the invention, an extract from *Lycium barbarum* or polysaccharide of *Lycium barbarum* may be used. This polysaccharide, which is referred to in the literature by the acronym LBP or as Goji, represents the most active compound present in the plant, typically in its fruits or berries (Wolfberry), typically Goji berries.

*Lycium barbarum* is a plant species in the form of a deciduous shrub belonging to the Solanaceae family. This plant produces red and/or purple fruits commonly known as Goji berries.

A suitable vegetal extract for the uses of the invention may be derived from roots, leaves, fruits, or flowers of *Lycium barbarum*, or from two or more of these parts of the plant. Preferably, the extract derives or is obtained from *Lycium barbarum* fruits or berries.

According to some embodiments, the vegetal extract of the invention is obtained by extraction from plant parts, in particular the fruits, using a physiologically acceptable or edible solvent as an extraction means. Within the scope of the invention, the term "edible" means a physiologically acceptable solvent that is fit to be eaten by a human being.

A solvent suitable for obtaining the vegetal extract is a physiologically acceptable and/or edible liquid, wherein the biologically active components are soluble, and wherein they do not undergo a significant alteration and such as to compromise the biological activity.

In some embodiments the solvent is of the hydrophilic type, and is selected from water, ethanol, ethyl acetate, or mixtures thereof.

It is possible to obtain a vegetal extract from *Lycium barbarum* fruits using conventional extraction techniques, for example by maceration or solid-liquid techniques suitable for separating/extracting one or more biologically active components from the vegetable tissues of plants and fruits thereof. It is also possible to carry out the extraction using supercritical $CO_2$.

In certain embodiments, the extraction of one or more biologically active components takes place by maceration of a vegetable portion or matrix in a suitable solvent, for example a hydroalcoholic mixture.

For example, a suitable extraction provides that *Lycium barbarum* fruits are immersed in a suitable solvent, such as a water-ethanol mixture, for a time suitable to enrich the solvent in one or more biologically active components. In certain embodiments, the maceration time may vary between 1 and 48 hours. The extraction of the biologically active components present in the vegetal tissues of the plant by the solvent may thus take place by diffusion and osmosis.

One of the most active components extractable from *Lycium barbarum*, in particular from its fruits, is the *Lycium barbarum* polysaccharide, commonly referred to in the literature as LBP and also identified with the abbreviation G below.

In the formulation of the composition of the invention it is possible to use a *Lycium* barbarum extract and/or the LBP polysaccharide.

The LBP polysaccharide may contain one or more of the monosaccharides arabinose, rhamnose, xylose, mannose, galactose, and glucose, and typically contains all of them. Galacturonic acid and amino acids may be present in the LBP polysaccharide composition.

Typically, the LBP polysaccharide is of natural or vegetable origin, however it can also be of synthetic origin, i.e. obtained through a chemical synthesis process. Typically, the extract obtained from *Lycium barbarum* can be fluid, soft, or dry. For example, in the fluid extract 1 mL of extract contains biologically active components soluble in 1 g of vegetable drug, in the soft extract the solvent is partially evaporated, specifically until the extract wets a filter paper, in the dry extract the solvent is evaporated almost completely to obtain a powder.

In certain embodiments, the extraction is performed using a weight ratio between solvent and vegetal matrix of between 1:10 and 10:1.

Typically, *Lycium barbarum* is also identified herein as Goji, and the extract originates or may be obtained from Goji berries.

Further methods to obtain *Lycium barbarum* vegetal extract for the uses of the invention include extraction techniques by digestion, infusion, squeezing, decoction, leaching, counter-current extraction, soxhlet, extraction with supercritical gases or ultrasounds.

In some embodiments, the *Lycium barbarum* extract, obtained according to any one of the embodiments described herein, is a fermented extract.

A further component of the composition of the invention is a *Moringa oleifera* extract, a plant belonging to the Moringaceae family.

A suitable vegetal extract for the uses of the invention may be derived from the roots, leaves, fruits, or flowers of *Moringa oleifera*, or from two or more of these parts of the plant.

Within the scope of the present description, *Moringa oleifera* is also referred to as *Moringa* and identified with the abbreviation M.

According to some embodiments, the vegetal extract of the invention is obtained by extraction from *Moringa oleifera* leaves, using a physiologically acceptable or edible solvent as an extraction means.

A solvent suitable for obtaining the vegetal extract is a physiologically acceptable and/or edible liquid, wherein the biologically active components are soluble, and wherein they do not undergo a significant alteration and such as to compromise the biological activity.

In some embodiments, the solvent is of the hydrophilic type and is selected from water, ethanol, ethyl acetate, or mixtures thereof. A preferred solvent is of the hydroalcoholic type.

A vegetal extract from *Moringa oleifera* may be obtained using conventional extraction techniques, for example using solid-liquid techniques suitable for separating/extracting one or more biologically active components from the vegetal tissues of the plant, or even with supercritical $CO_2$.

In certain embodiments, the extraction of one or more biologically active components takes place by maceration of a vegetable portion or matrix in a suitable solvent, for example a hydroalcoholic mixture.

As an example, *Moringa oleifera* leaves are immersed in a suitable solvent, typically a water-ethanol mixture, for a time suitable to enrich the solvent in one or more biologically active components present in the treated leaves. Under these conditions, the extraction of the biologically active components present in the vegetable tissues of the plant by the solvent takes place by diffusion and osmosis. The extraction may also be performed by macerating *Moringa oleifera* leaves and keeping them in contact with the solvent for a time suitable for obtaining the extraction of an effective amount of one or more of the biologically active components. In certain embodiments the maceration time may vary between 1 and 48 hours.

For example, the biologically active components obtainable by extraction with hydroalcoholic solvent (50:50) comprise one or more of epigallocatechin gallate, quercetin, genistein, caffeic acid esters, baicalein, morin, myricetin, rutin, biochanin a A, chrysin, taxifolin, fisetin, octyl/dodecyl gallates, anthraquinone, kaempferol, emodin.

In some embodiments, the *Moringa oleifera* extract obtained according to any one of the embodiments described herein is a fermented extract.

Within the scope of the invention, the term phytoextract designates an extract obtained by extraction from one of said plants or it refers to the LBP polysaccharide. Typically, the composition of the invention comprises an active amount of one or more biologically active components extracted from *Lycium barbarum* and *Moringa oleifera*.

According to some embodiments, both *Lycium barbarum* and *Moringa oleifera* extracts are fermented.

The composition of the invention may be authorized for trade as a drug, a medical device, or a dietary or nutritional supplement.

In some embodiments, the composition of the invention comprises a physiologically and/or pharmaceutically acceptable carrier, diluent or excipient.

Typically, the physiologically acceptable carrier of the composition of the invention is an excipient, carrier, or diluent suitable for topical application and/or oral administration.

Within the present scope, the term "carrier" refers to an excipient, carrier, diluent, or adjuvant that may be present in the composition of the invention. Any carrier and/or excipient suitable for the desired form of preparation for administration is contemplated in the uses of the vegetal extract or active principles therein present described herein.

In certain embodiments, the composition of the invention contains components of a vegetable origin that are biologically active and substantially free of side effects, when administered orally or locally.

The pharmaceutically and/or physiologically acceptable carrier, diluent or excipient may be selected based on the route of administration for which the resulting pharmaceutical composition is intended.

In other embodiments, the composition is for topical use and is applied to the skin.

In some embodiments, the route of administration of the composition of the invention is the topical one.

In these cases, the composition of the invention may be in the form of an emulsion, cream, salve, ointment, lotion.

In cosmetic applications, for example in preventing or treating photoaging from exposure to the sun's rays, it is possible to apply a cosmetically active amount of composition of the invention to the affected skin area, one or more times a day, conveniently for a period of at least 2-3 months.

According to another aspect of the invention, a cosmetic treatment method is provided that comprises the application to the scalp of an effective amount of a composition of the type described above.

The composition for topical application may be in solid, semi-solid, or fluid form.

Suitable formulations in solid form include creams, gels, salves, pastes, ointments. In other embodiments, the formulation for local administration is in fluid form, for example in the form of lotions, gels, shampoos, suspensions, emulsions.

In some embodiments, the compositions of the invention may comprise excipients commonly used in the formulation of cosmetic or pharmaceutical preparations for local use, such as preservatives, bactericidal agents, stabilizers, emulsifiers, buffers, wetting agents, colouring agents, and other excipients commonly used in the cosmetic/pharmaceutical preparation techniques.

In one embodiment, the formulation for local application is in the form of an emulsion containing the extract carried by a suitable excipient. In some embodiments, the composition for topical application comprises an excipient of the hydroxymethylcellulose type and/or gelling agents with HLB suitable for the formulation and substances.

The composition may be in a form for oral administration.

The compositions for oral administration may be in the solid or liquid form. Typical solid form compositions comprise tablets, capsules, powders, granules, pills, jellies. Typical liquid form compositions comprise solutions, emulsions, suspensions, syrups. All the compositions also comprise controlled-release forms thereof. The tablets generally comprise a suitable carrier or excipient wherein the vegetal extract is dispersed, typically in the dry form.

In this case, suitable excipients contained in the formulation are cellulose derivatives, such as hydroxymethylcellulose, hydroxypropylmethylcellulose, methylcellulose, hydroxypropylcellulose, hydroxyethylcellulose, carboxyethylcellulose, ethylhydroxyethylcellulose, cellulose acetate butyrate, cellulose acetate phthalate, and mixtures thereof.

Further examples of suitable excipients comprise polymers belonging to the family of lactams, such as pyrrolidone and derivatives thereof, such as polyvinylpyrrolidone, polyvinylpolypyrrolidone, and mixtures thereof, inorganic salts such as calcium or dicalcium phosphate, lubricants, such as magnesium stearate, triacylglycerols, and mixtures thereof.

The biologically active components or extracts contained in the composition of the invention may be present in variable amounts, for example ranging from 0.0001% by weight to 50% by weight, from 0.1% by weight to 20% by weight, typically from 0.5 to 5% by weight.

In accordance with certain embodiments, the composition of the invention further comprises one or more active substances, such as vitamins, minerals, micronutrients, and other active substances.

In accordance with some embodiments, the composition for oral administration is a functional food, a nutraceutical composition, a dietary product, a supplement or nutritional product, or a medical device.

Functional food means any modified food or food ingredient that can provide a benefit or protection against a drawback or a physiological condition, besides the traditional nutrients it contains.

Nutraceutical product means a product isolated or purified from edible substances. A nutraceutical is such when it is shown to have a physiological benefit or to provide protection against a drawback or physiological disorder.

Dietary or nutritional supplement means a product that contains a vitamin, mineral, vegetal extract, amino acid, metabolite, extract, concentrate, or mixtures of these ingredients.

The amount administered and the frequency of administration of the composition will depend on the nature and severity of the condition to be treated.

The present invention will now be described with reference to the following examples which are provided for mere illustrative purposes and are not to be intended as limiting the present invention.

Example 1

| Film-coated tablet | |
|---|---|
| Component | Amount (mg) |
| Fermented N-acetyl-L-cysteine | 75-225 |
| N-Acetyl-D-glucosamine | 75-225 |
| *Moringa oleifera* Seeds Dry Extract | 50-150 |
| *Lycium barbarum* L. Fruits Dry Extract | 25-75 |
| Vitamin E Acetate 50% | 23-70 |
| Zeaxanthin | 20-60 |
| L-Selenomethionine | 6-17 |
| Copper Gluconate | 4-11 |
| Biotin | 0.03-0.1 |
| Microcrystalline Cellulose | 110-330 |
| Hydroxypropylcellulose | 15-45 |
| White Film-Forming Polymer | 8-25 |
| Cross-linked Sodium Carboxymethyl Cellulose | 8-24 |
| Magnesium Stearate (vegetal origin) | 4-12 |
| Silicon Dioxide | 2-6 |
| Glycerol (Ph. Eur) 99.5% | 1.2-3.7 |
| Yellow Iron Oxide Pigment (E172) | 2.3-6.8 |
| Red Iron Oxide Pigment (E172) | 1-3 |

Example 2

| Tablet | |
|---|---|
| Component | Amount (mg) |
| *Moringa oleifera* Seeds Dry Extract | 85.7-114.3 |
| Goji Fruits Dry Extract | 42.9-57.1 |
| Mannitol | 90-120 |
| Microcrystalline Cellulose | 45-60 |
| Pregelatinized Starch | 14.1-18.8 |
| Sodium Starch Glycolate Type A | 13.5-18.0 |
| Magnesium Stearate | 1.5-2.0 |
| Hydroxypropylmethylcellulose | 6.3-8.4 |
| Titanium Dioxide | 1.1-1.4 |

Example 3

| Cream | |
|---|---|
| Component | Amount (mg) |
| Polisorbate 60 | 0.8-2.3 |
| Sorbitan Monostearate | 1-3 |
| Benzyl Alcohol | 0.5-1.5 |
| Octyldodecanol | 6.5-19.5 |
| *Moringa oleifera* Seeds Dry Extract | 0.5-1.5 |
| Goji Fruits Extract | 0.3-0.8 |
| Cetyl Palmitate | 1.5-4.5 |
| Cetyl Stearyl Alcohol | 5-15 |
| Water | q.s. to 100 g |

Example 4

| Solution | |
|---|---|
| Component | Amount (mg) |
| Ethyl Alcohol | 15.1-21.7 |
| Disodium EDTA Dihydrate | 0.03-0.09 |
| PEG-40 Hydrogenated Castor Oil | 0.8-2.3 |
| *Moringa* Seeds Extract | 1-3 |
| Goji Fruits Extract | 1-3 |
| Ethoxydiglycol | 0.3-0.8 |
| Water | q.s. to 100 g |

Example 5

| Fluid Emulsion | |
|---|---|
| Component | Amount (mg) |
| Allantoin | 0.1-0.3 |
| EDTA Disodium Dihydrate | 0.1-0.2 |
| Xanthan Gum | 0.1-0.2 |
| *Moringa oleifera* Seeds Extract | 0.1-5.0 |
| Crosslinked-polymer-6 polyacrylate | 0.3-0.8 |
| Olivoil Avenate Emulsifier | 2-6 |
| Meadowfoam Seed Oil | 1.5-4.5 |
| Squalan | 1.5-4.5 |
| Di-n-butyl Adipate | 3-9 |
| Cetiol Ultimate | 1-3 |
| Glyceryl Stearate | 0.8-2.3 |
| Cetyl Stearyl Alcohol | 0.8-2.3 |
| Acticire | 0.8-2.3 |
| *Lycium barbarum* Fruits Extract | 0.05-5.0 |
| Natural Vitamin E | 0.1-0.3 |
| Stearyl Glycyrrhetinate | 0.1-0.2 |
| Dimethicone | 0.5-1.5 |
| Glycerol | 1.5-4.5 |
| Euxyl PE9010 | 0.5-1.5 |
| O-Cymen-5-ol | 0.1-0.2 |
| Zeastat ® | 0.7-2 |
| Perfume | 0.3-0.8 |
| 90% Lactic Acid | 0.1-0.3 |
| Water | q.s. to 100 g |

Example 6

Comparative Experimental Tests

Object of the Experimental Work

The object of the present in vitro study is to study the effects of two vegetal extracts, *Moringa* Extract and Goji Extract, respectively, tested alone and in combination, on proliferation, protection, and recovery from oxidative stress induced in cell lines.

Materials

Samples Tested

| INTERNAL NAME | *Moringa* Extract | Goji Extract | *Moringa* + Goji Combination |
|---|---|---|---|
| UNIQUE IDENTIFICATION NAME | M | G | M + G |
| BATCH | MFG: 10/17 | MFG: 13/01/17 | / |
| STORAGE | rt | rt | rt |
| CONCENTRATIONS | 10-25-50-100-200 µg/mL | 10-25-50-100-200 µg/mL | 2:1:<br>200M + 100G µg/mL<br>100M + 50G µg/mL<br>50M + 25G µg/mL<br>25M + 12.5G µg/mL |

Reagents and Instruments Used

| REAGENTS | SUPPLIER |
|---|---|
| RPMI-1640 MEDIUM | SIGMA, R0883 |
| FETAL BOVINE SERUM | SIGMA, F7524 |
| Gentamicin Solution | SIGMA, G1272 |
| L-glutamine | SIGMA, G7513 |
| 30% Hydrogen Peroxide | SIGMA, 216763 |
| 2',7'-Dichloro-fluorescein Diacetate | SIGMA, 35845 |
| Dimethylsulfoxide | SIGMA, D2438-50ML |
| Dulbecco's Phosphate Buffered Saline | SIGMA, D8537 |
| MTT | SIGMA- Aldrich, M2128 |
| Penicillin-Streptomycin | SIGMA, P0781 |
| α-Tocopherol | SIGMA, T3251 |

| INSTRUMENTS | SUPPLIER |
|---|---|
| 15 L Digital water bath from +5° C. to +100° C. (Mod: Swbd1, BS-SWB2D) | Stuart |
| Balance (Model XS204) | Mettler Toledo |
| Laminar flow cabinet (Model Gemini) + UV lamp with anti-reflex equipment | SterilManifacturingDivision |
| HeraCell $CO_2$ incubator (Model150 ADV) | ThermoScientific |
| Horizontal freezer −85° C. ULT130, 120 L (Mod: Labfrost, MME-TE21140) | Elcold |
| Bürker counting chamber w/clamps (DI-DA-443/3) | Carlo Erba |
| Automated Microplate Reader (EL 808) | BioTek |
| Vortex | Arhos160-PBI International |

Biological Models Used

Cultures of Human Keratinocytes

It is used the immortalized line of human keratinocytes NCTC 2544 (Perry V P et al., 1957), maintained in sterile culture flasks (25 cm³), incubated at 37° C., in a 5% $CO_2$ humidified atmosphere in RPMI culture medium added with 10% fetal bovine serum (FBS), 2 mM glutamine, in the presence of 1% penicillin and streptomycin and 0.1% gentamicin.

The 1:3 split is performed every 2 days, upon reaching the monolayer, by washing with 1×PBS ($Ca^{2+}$ and $Mg^{2+}$ free phosphate buffer) and detaching the cells with a trypsin-EDTA solution at 37° C. for 2 minutes. The cells were maintained in 25 cm³ sterile culture flasks and incubated at 37° C. in a 5% $CO_2$ humidified atmosphere.

| ICLC CATALOG CODE | HL97002 |
|---|---|
| DEPOSITOR | Prof. M. Ferro, DIMES, General Pathology, University of Genoa, Italy |
| BIBLIOGRAPHICAL REFERENCES | Arch Dermatol Res 1976; 256 (3): 255-260-PMID: 990102<br>Arch Dermatol Res 1976; 261 (1): 27-31 |

Controls

MTT Assay

POSITIVE CONTROL: Non-treated cells in RPMI added with 10% fetal bovine serum (FBS), 2 mM glutamine, in the presence of 1% penicillin and streptomycin and 0.1% gentamicin and maintained in 25 cm² (96 well) culture plates at 37° C. and 5% $CO_2$.

MTT-Induced Oxidative Stress Test

NEGATIVE CONTROL: Non-treated cells in RPMI added with 10% fetal bovine serum (FBS), 2 mM glutamine, in the presence of 1% penicillin and streptomycin and 0.1% gentamicin and maintained in 25 cm² (96 well) culture plates at 37° C. and 5% $CO_2$ (in the dark).

POSITIVE CONTROL: Cells treated for 2 hrs with 1 mM hydrogen peroxide in RPMI added with 10% fetal bovine serum (FBS), 2 mM glutamine, in the presence of 1% penicillin and streptomycin and 0.1% gentamicin and maintained in 25 cm² (96 well) culture plates at 37° C. and 5% $CO_2$ (in the dark).

Methods

MTT (Cell Proliferation) on Human Keratinocyte Cell Line NCTC2544

Principle of the Method

The MTT assay (3-(4,5-dimethylthiazol-2-yl)-2,5-diphenyltetrazolium bromide) is a colorimetric assay used to assess cell proliferation in vitro, since it allows to measure cell proliferation and viability by assessment of the mitochondrial activity [162]. This method is very useful to measure cell growth following treatment with mitogenic agents, antigenic stimuli, growth factors, and for cytotoxicity studies.

The assay involves the use of a chromogenic oxidizing agent, MTT, consisting of a polycyclic system ($C_{18}H_{16}BrN_5S$) including a tetrazole ring that can be easily reduced by mitochondrial dehydrogenases or other electron transport systems, forming, by opening the tetrazole ring, a nitrogen chromogen compound called formazan. Formazan forms insoluble crystals in the intracellular environment, to which membranes are substantially impermeable: the molecule entry into the cell is therefore allowed, but the exit of the product is not allowed, provided it has been properly metabolized, i.e. if the transport chains electronic are still metabolically active.

Formazan crystals are then solubilized in dimethylsulfoxide (DMSO), thus causing the solution to shift from yellow to dark blue-violet.

Experimental Procedure

The assay was conducted according to Mosmann's method (1983), with some minor modifications. The human keratinocytes NCTC2544 were seeded in a 96-well plate at the density of $51*10^4$ cells/well and incubated at 37° C., with 5% of $CO_2$, until about 80% confluence was reached.

Subsequently, the cells were incubated for 24-48-72 hours with the active compounds to be tested at the following concentrations: 10-25-50-100 and 200 µg/mL for Moringa and Goji extract, respectively. The two active ingredients were also tested in combination in a 2:1 ratio at the following concentrations: 25 µg/mL Moringa and 12.5 µg/mL Goji; 50 µg/mL Moringa and 25 µg/mL Goji; 100 µg/mL Moringa and 50 µg/mL Goji, and 200 µg/mL Moringa and 100 µg/mL Goji.

The dilutions were prepared starting from sterile filtered 1000× stocks in complete medium and using RPMI medium added with 10% fetal bovine serum (FBS), 2 mM glutamine, in the presence of 1% penicillin and streptomycin and 0.1% gentamicin. Untreated cells were used as a positive control.

At the end of all treatments, the medium was drawn and replaced with 100 µL of an MTT solution (Sigma-Aldrich, St. Louis, Mo., USA) 0.5 mg/mL in complete culture medium.

After 3 hours of incubation at 37° C., the medium was drawn and the formazan crystals were solubilized with 100 µL of DMSO per well (Sigma-Aldrich, St. Louis, Mo., USA). The plate, covered with aluminium foil, was placed on a mechanical stirrer (Arhos 160-PBI International, Milan, Italy) at 120 rpm for 15 minutes at room temperature.

The absorbance of the coloured solution was measured using a spectrophotometric microplate reader (BioTek Instruments Inc., BadFriedrichshall, Germany) at a wavelength of 570 nm (reference wavelength at 630 nm).

The data were expressed as cell viability percentage with respect to control cells (ctr), according to the following formula:

% cell viability/ctr=(Abs sample/Abs ctr)*100

All analyses were performed at least twice in duplicate.
Study of Protection Against Induced Oxidative Stress on Human Keratinocyte Line NCTC2544

Principle of the Method

Studies conducted in 2005 by Rajapakse and collaborators (2005) highlighted the possibility of exploiting a widely used and versatile method as the MTT assay for studying the in vitro antioxidant activity of active compounds. Specifically, by this method it is possible to study the protective effects of these compounds on cells subsequently subjected to oxidative stress. The induction of oxidative stress is performed by incubation with hydrogen peroxide, an agent that induces oxidative damage production in cells through the formation of ROSs. The possible protective effects may be determined by assessment of post-oxidative stress cell viability of cells pre-treated/pre-exposed to the active compounds to be tested, in comparison to cells subjected to the same oxidative stress. A greater cell viability will correspond to a protective effect of the tested compounds.

Experimental Procedure

The assay was conducted according to the method described by Coda and collaborators (Coda et al., 2012), with some modifications.

Human keratinocytes NCTC2544 were seeded in a 96-well plate at a density of $5*10^4$ cells/well and incubated at 37° C., with 5% $CO_2$, until about 80% confluence was reached.

Subsequently, the cells were incubated for 16 hours with the active compounds to be tested, and the respective controls, at the following concentrations: 100 µg/mL for Moringa extract and 50 µg/mL for Goji extract. The two active ingredients were also tested in combination in a 2:1 ratio at the following concentrations: 100 µg/mL Moringa and 50 µg/mL Goji.

The dilutions were prepared starting from sterile filtered 1000× stock in DMSO and using RPMI medium added with 2.5% fetal bovine serum (FBS), 2 mM glutamine, in the presence of 1% penicillin and streptomycin and 0.1% gentamicin.

Cells treated with 1 mM $H_2O_2$ were used as positive control; while cells maintained in the culture medium alone (RPMI 2.5% FCS) were used as negative control.

Alpha tocopherol was tested as a reference antioxidant at a concentration of 250 and 500 µg/mL, respectively.

At the end of the 16 hours pre-treatment, the cells were washed with 1×PBS and incubated for 90 minutes with a 1 mM solution of $H_2O_2$ (Sigma-Aldrich, St. Louis, Mo., USA) in serum free medium, in the dark, at 37° C., with 5% $CO_2$.

Once the oxidative stress induction phase was ended, the cell viability of the various samples was assessed according to the method described in point 4.1.2 (MTT Assay).

The data were expressed as cell viability percentage with respect to non-stressed control cells (ctr), according to the following formula:

% cell viability/ctr=(Abs sample/Abs ctr)*100

All analyses were performed at least twice in duplicate.
Study of Recovery Activity from Oxidative Stress Induced on Human Keratinocyte Line NCTC2544

Principle of the Method

Studies conducted in 2005 by Rajapakse and collaborators (2005) highlighted the possibility of exploiting a widely used and versatile method as the MTT assay for studying the in vitro antioxidant activity of active compounds. Specifically, by this method it is possible to study the protective effects of these compounds on cells subsequently subjected to oxidative stress. The induction of oxidative stress is performed by incubation with hydrogen peroxide, an agent that induces oxidative damage production in cells through the formation of ROSs. The possible protective effects may be determined by assessment of post-oxidative stress cell viability of cells pre-treated/pre-exposed to the active compounds to be tested, in comparison with cells subjected to the same oxidative stress. A greater cell viability will correspond to a protective effect of the tested compounds.

Experimental Procedure

The assay was conducted according to the method described by Coda and collaborators (Coda et al., 2012), with some modifications.

Human keratinocytes NCTC2544 were seeded in a 96-well plate at the density of $5*10^4$ cells/well and incubated at 37° C., with 5% $CO_2$, until about 80% confluence was reached.

The cells were incubated for 90 minutes with a 1 mM $H_2O_2$ solution (Sigma-Aldrich, St. Louis, Mo., USA) in serum free medium, in the dark, at 37° C. and 5% $CO_2$. Subsequently, the cells were washed with 1×PBS and incubated for 16 hours with the active compounds to be tested, and the respective controls, at the following concentrations: 50-100 µg/mL for Moringa extract and 25-50 µg/mL for Goji extract. The two active ingredients were also tested in combination in a 2:1 ratio at the following concentrations: 50 µg/mL Moringa and 25 µg/mL Goji; 100 µg/mL Moringa and 50 µg/mL Goji.

The dilutions were prepared starting from sterile filtered 1000× stock in DMSO and using RPMI medium added with 2.5% fetal bovine serum (FBS), 2 mM glutamine, in the presence of 1% penicillin and streptomycin and 0.1% gentamicin.

Cells treated with 1 mM $H_2O_2$ were used as positive control; while cells maintained in the culture medium alone (RPMI 2.5% FCS) were used as negative control.

Alpha tocopherol was tested as a reference antioxidant at a concentration of 250 and 500 µg/mL, respectively.

At the end of the 16 hours pre-treatment, the cell viability of the various samples was assessed according to the method described in point 4.1.2 (MTT Assay).

The data were expressed as cell viability percentage with respect to non-stressed control cells (ctr), according to the following formula:

% cell viability/ctr=(Abs sample/Abs ctr)*100

All analyses were performed at least twice in duplicate.

Results

MTT (Cell Proliferation) on Human Keratinocyte Line NCTC2544

After 24 hours treatment (Table 1), none of the extracts tested produced cytotoxicity (cell viability <80%) on the human keratinocyte NCTC2544 cell line, and the cell viability values found are similar to those of the untreated control. Significant proliferative activity ($p<0.05$) of Goji extract at a concentration of 10 µg/mL is to be reported.

After 48 hours treatment, both extracts at the highest treatment concentrations (200 and 100 µg/mL) show a slight decrease in cell viability, although the values remain above or similar to 80% cell viability (Table 1). A similar situation is found when the Goji extract is tested at 50 and 25 µg/mL concentrations, and when the two extracts are tested in combination (Table 1).

It is interesting to note that the Moringa extract tested at the lowest concentrations (25 and 10 µg/mL) shows proliferative activity on human keratinocytes after 48 hours of treatment.

The situation remains similar following the treatments with extracts and combinations thereof for 72 h. A cytotoxic effect (% viability lower than 80%) occurs when the cells are treated with the highest concentrations (200 and 100 µg/mL) of the two extracts. In particular, for Goji extract this effect persists up to a concentration of 25 µg/mL.

TABLE 1

| | | Cell viability. | | |
|---|---|---|---|---|
| | Concentrations Tested | % Cell Viability/Control ± SEM | | |
| | (µg/mL) | 24 h | 48 h | 72 h |
| Control* | | 100.00 ± 3.21 | 100.00 ± 7.17 | 100.00 ± 6.65 |
| Moringa | 200 µg/mL | 102.58 ± 1.13 | 84.06 ± 0.37[c] | 77.49 ± 1.54[f] |
| Extract | 100 µg/mL | 102.82 ± 1.71 | 80.58 ± 2.22[d] | 66.09 ± 4.97[g] |
| | 50 µg/mL | 100.20 ± 0.50 | 102.09 ± 1.17 | 80.24 ± 3.88[d] |
| | 25 µg/mL | 95.55 ± 1.59 | 111.45 ± 0.21[e] | 81.11 ± 2.60[d] |
| | 10 µg/mL | 100.81 ± 2.55 | 109.82 ± 6.78 | 84.58 ± 4.67[c] |
| Goji | 200 µg/mL | 101.12 ± 5.94 | 82.05 ± 6.76[d] | 39.14 ± 7.35[h] |
| Extract | 100 µg/mL | 104.63 ± 1.37 | 85.26 ± 16.97[d] | 25.84 ± 0.03[i] |
| | 50 µg/mL | 101.69 ± 5.68 | 77.55 ± 7.457[d] | 72.87 ± 3.08[f] |
| | 25 µg/mL | 99.85 ± 2.54 | 78.87 ± 7.657[d] | 72.57 ± 0.51[f] |
| | 10 µg/mL | 106.13 ± 3.87[a] | 93.46 ± 2.777 | 78.48 ± 8.41[d] |
| Combination | 100 + 50 µg/mL | 90.21 ± 0.29[b] | 80.16 ± 2.19[d] | 84.31 ± 3.50[c] |
| of Moringa | 50 + 25 µg/mL | 98.42 ± 0.29 | 81.98 ± 5.677[d] | 79.92 ± 1.95[d] |
| extract + | 200 + 100 µg/mL | 97.12 ± 2.79 | 71.54 ± 8.377[d] | 83.33 ± 2.05[c] |
| Goji extract (2:1) | 25 + 12.5 µg/mL | 98.56 ± 1.97 | 89.87 ± 6.50 | 74.09 ± 4.90[f] |

% Cell viability on human keratinocytes NCTC2544 following treatment for 24, 48 and 72 h with 10-25-50-100 and 200 µg/mL of Moringa and Goji extracts, and in combination in a 2:1 ratio at the following concentrations: 25 µg/mL Moringa and 12.5 µg/mL Goji; 50 µg/mL Moringa and 25 µg/mL Goji; 100 µg/mL Moringa and 50 µg/mL Goji; and 200 µg/mL Moringa and 100 µg/mL di Goji

[a-i]Values with different superscript letters differ significantly ($p < 0.005$).

Study of Protection Against Oxidative Stress Induced on the Human Keratinocyte Line NCTC2544

Incubation of human keratinocytes for 16 hrs with *Moringa* and Goji extracts, alone or in combination, proved to be able to protect cells from oxidative stress induced by application of hydrogen peroxide (1 mM $H_2O_2$).

In particular, at the same concentration, the *Moringa* extract was significantly more effective than the Goji extract (FIG. 1) and this effect is comparable to that of alpha tocopherol tested at 250 and 500 µM, respectively.

Furthermore, when the two extracts were tested in combination, a significant (p<0.05) synergistic effect on cell viability protecting activity following oxidative stress was recorded, mainly at the highest concentrations (*Moringa* 100 µg/mL and Goji 50 µg/mL), as shown in Table 2.

TABLE 2

Protection from oxidative stress

| Extract | % Viability | T test (vs combo) |
|---|---|---|
| *Moringa* 100 µg/mL | 62.549 | p < 0.05 |
| Goji 50 µg/mL | 61.516 | p < 0.05 |
| *Moringa* 100 µg/mL + Goji 50 µg/mL | 67.011 | |

These data are shown in FIG. 1 that illustrate the cell viability percentage in human keratinocytes NCTC2544 following induction of oxidative stress induced with 1 mM $H_2O_2$. The cells were previously incubated for 16 hrs with 100 and 50 µg/mL of *Moringa* and Goji extract, and in combination in a 2:1 ratio: 100 µg/mL *Moringa* and 50 µg/mL of Goji.

* (p<0.05)

Study of the Recovery Activity from Oxidative Stress Induced on the Human Keratinocyte Line NCTC2544

The incubation of human keratinocytes for 16 hrs with *Moringa* and Goji extracts, alone or in combination, proved to be able to facilitate the recovery of cell viability following the induction of oxidative stress induced by application of hydrogen peroxide (1 mM $H_2O_2$).

In particular, at the same concentration, both extracts were able to significantly induce (p<0.005) cell viability of human keratinocytes following induced oxidative stress (FIG. 2), and this effect is comparable to that of alpha tocopherol tested at 250 and 500 µM, respectively.

Furthermore, when the two extracts are tested in combination, there is a significant (p<0.05) synergistic effect on the cell viability protecting activity, mostly at the highest concentration (*Moringa* 100 µg/mL and Goji 50 µg/mL). The data are shown in Table 3.

TABLE 3

Post-oxidative stress recovery

| Extract | % Viability | T test (vs combo) |
|---|---|---|
| *Moringa* 100 µg/mL | 41.083 | p < 0.05 |
| Goji 50 µg/mL | 47.361 | p < 0.05 |
| *Moringa* 100 µg/mL + Goji 50 µg/mL | 60.055 | |

TABLE 3-continued

Post-oxidative stress recovery

| Extract | % Viability | T test (vs combo) |
|---|---|---|
| *Moringa* 50 µg/mL | 44.948 | p < 0.01 |
| Goji 25 µg/mL | 45.772 | p < 0.01 |
| *Moringa* 50 µg/mL + Goji 25 µg/mL | 52.619 | |

Figure 2:
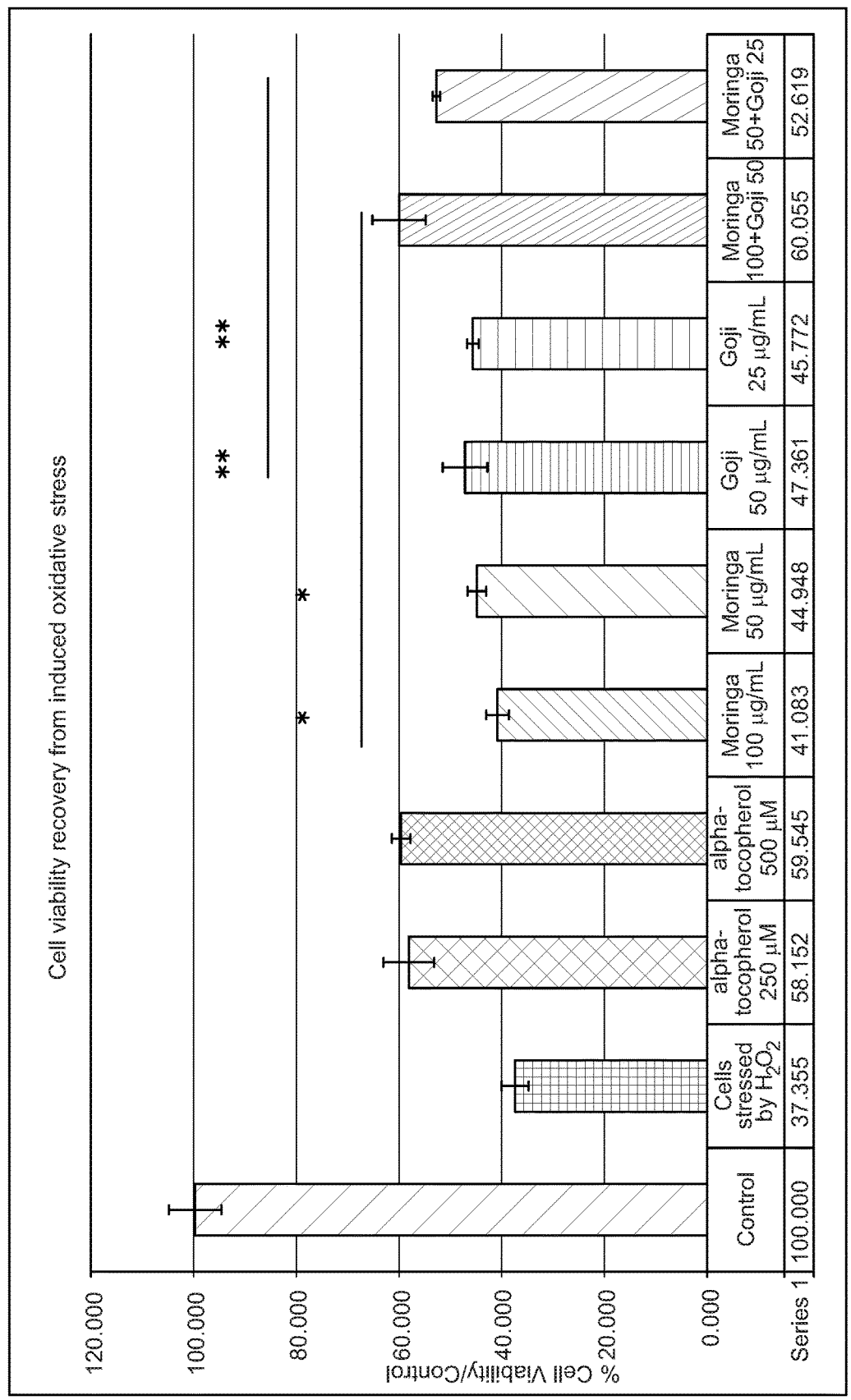
FIG. 2 shows bar graphs showing cell viability recovery following induced oxidative stress according to Example 6.

Specific statistics (t tests) deriving from the comparison between single and combos As shown in FIG. 2, the protection exercised by the combination of the two active ingredients was comparable to that exerted by alpha tocopherol, used as a reference antioxidant.

Specifically, FIG. 2 illustrates cell viability recovery following induced oxidative stress by highlighting the percentage of cell viability on human keratinocytes NCTC2544 following induction of oxidative stress induced with 1 mM $H_2O_2$. Following the induction of oxidative stress, the cells were incubated for 16 hrs with 100 and 50 µg/mL of *Moringa* and Goji extract, and in combination in a 2:1 ratio: 50 µg/mL *Moringa* and 25 µg/mL Goji; 100 µg/mL *Moringa* and 50 µg/mL Goji. *(p<0.05), **(p<0.01)

Statistic Analysis

All data were obtained at least in three replicates. The analysis of variance (ANOVA) was performed on processed data, followed by mean separation using the Student t-test, using GraphPad Prism version 7.00 for Windows, GraphPad Software (San Diego Calif. USA, www.graphpad.com).

BIBLIOGRAPHICAL REFERENCES

Mosmann T, 1983. Rapid Colorimetric Assay for Cellular Growth and Survival: Application to Proliferation and Cytotoxicity Assays. J Immunol Methods 65(1-2), 55-63.

Coda R, Rizzello C G, Pinto D, Gobbetti M, 2012. Selected Lactic Acid Bacteria Synthesize Antioxidant Peptides during Sourdough Fermentation of Cereal Flours. Appl Environ Microbiol 78(4), 1087-1096.

Example 7

For the study of the synergistic activity of the combination of the two *Moringa* and Goji extracts, two types of in vitro assessments were performed on the cell line:
  1—Antioxidant activity, by hydrogen peroxide as an agent capable of inducing a high oxidative stress that leads to cellular apoptosis, in which the extracts were tested (alone or in combination) in the recovery-restoring damage- and protection against oxidative stress;
  2—Protection activity on UVA damage, in which the extracts were evaluated, alone or in combination, using the method indicated below.

Assessment of Antioxidant Activity

Materials and Methods

Materials and methods are the same as described in Example 6 and are referenced to here.

Results

In order to better express the biological activity results for the oxidative stress test with $H_2O_2$, data are expressed in the table as % of improvement with respect to stressed cells, as reported in other literature studies (e.g. https://www.ncbi.nlm.nih.gov/pmc/articles/PMC5122827/).

The results, obtained following $H_2O_2$ damage followed by treatment with the extracts, show how the extracts alone have an activity of restoration and recovery of the damage resulting in apoptosis induced by oxidative stress, with a synergistic effect for the ratios shown in the table below.

Recovery

| M/G | Extract | Vs $H_2O_2$ | |
|---|---|---|---|
| | | % Viability | Synergy |
| | Moringa 50 µg/mL | 87.268 | |
| | Goji 150 µg/mL | 113.824 | |
| 1:3 | Moringa 50 µg/mL + Goji 150 µg/mL | 126.836 | +26.295 |
| | Moringa 150 µg/mL | 116.12 | |
| | Goji 50 µg/mL | 117.94 | |
| 3:1 | Moringa 150 µg/mL + Goji 50 µg/mL | 125.02 | +7.99 |
| | Moringa 50 µg/mL | 87.268 | |
| | Goji 250 µg/mL | 123.815 | |
| 1:5 | Moringa 50 µg/mL + Goji 250 µg/mL | 124.303 | +18.755 |
| | Moringa 250 µg/mL | 113.615 | |
| | Goji 50 µg/mL | 117.937 | |
| 5:1 | Moringa 250 µg/mL + Goji 50 µg/mL | 123.420 | +7.64 |
| | Moringa 50 µg/mL | 87.268 | |
| | Goji 350 µg/mL | 125.999 | |
| 1:7 | Moringa 50 µg/mL + Goji 350 µg/mL | 119.726 | +13.095 |

As regards the protection from oxidative stress, wherein treatment with the extracts, alone or in combination according to particular ratios, was carried out before incubation with hydrogen peroxide, the results show the synergistic effect of the combinations.

Protection

| M/G | Extract | Vs $H_2O_2$ | |
|---|---|---|---|
| | | % Viability | Synergy |
| 1:3 | Moringa 50 µg/mL + Goji 150 µg/mL | 108.55 | +11.28% |
| 3:1 | Moringa 150 µg/mL + Goji 50 µg/mL | 110.417 | +12.705% |
| 5:1 | Moringa 250 µg/mL + Goji 50 µg/mL | 122.51 | +16.475% |

Assessment of Protective Activity Against UVA

Materials and Methods

Human Keratinocytes Cultures

It was used the immortalized line of human keratinocytes NCTC 2544 (Perry V P et al., 1957) maintained in sterile culture flasks (25 cm$^3$), incubated at 37° C., in a 5% $CO_2$ humidified atmosphere, in RPMI culture medium added with 10% fetal bovine serum (FBS), 2 mM glutamine, in the presence of 1% penicillin and streptomycin and 0.1% gentamicin.

The 1:3 split is performed every 2 days, upon reaching the monolayer, by washing with 1×PBS ($Ca^{2+}$ and $Mg^{2+}$ free phosphate buffer) and detaching the cells with a trypsin-EDTA solution at 37° C. for 2 minutes. The cells were maintained in 25 cm$^3$ sterile culture flasks and incubated at 37° C. in a 5% $CO_2$ humidified atmosphere.

| ICLC CATALOG CODE | HL97002 |
|---|---|
| DEPOSITOR | Prof. M. Ferro, DIMES, General Pathology, University of Genoa, Italy |
| BIBLIOGRAFIC REFERENCES | Arch Dermatol Res 1976; 256 (3): 255-260- PMID: 990102 Arch Dermatol Res 1976; 261 (1): 27-31 |

Controls

Negative control: Non-treated cells in RPMI added with 2.5% fetal bovine serum (FBS), 2 mM glutamine, in the presence of 1% penicillin and streptomycin and 0.1% gentamicin and maintained in 25 cm$^2$ culture plates (96 well) at 37° C. and 5% $CO_2$. Positive control: Stressed cells (UVA 10 J/cm$^2$) in RPMI added with 2.5% fetal bovine serum (FBS), 2 mM glutamine, in the presence of 1% penicillin and streptomycin and 0.1% gentamicin and maintained in 25 cm$^2$ (96 well) culture plates at 37° C. and 5% $CO_2$.

Study of Protection Against Stress Induced by UVA Rays

The assay was conducted according to the method described by Fiori and collaborators (Fiori et al., 2017), with some modifications.

Human keratinocytes NCTC2544 were seeded in a 96-well plate at a density of 5*10$^4$ cells/well and incubated at 37° C., with 5% $CO_2$, until about 80% confluence was reached.

Subsequently, the cells were incubated for 16 hours with the active compounds to be tested, and the respective controls, at the following concentrations: 150 and 250 µg/mL for Moringa extract and 50 µg/mL for Goji extract. The two active ingredients were also tested in combination in the following ratios: 3:1 and 5:1.

The dilutions were prepared starting from sterile filtered 1000× stock in DMSO and using RPMI medium added with 2.5% fetal bovine serum (FBS), 2 mM glutamine, in the presence of 1% penicillin and streptomycin and 0.1% gentamicin.

Non-stressed cells (no UVs) were used as negative control; while cells maintained in the culture medium alone (RPMI 2.5% FBS) and stressed respectively with UVA rays (10 J/cm$^2$) were used as positive control.

At the end of the 16 hours pre-treatment, the cells were washed with 1×PBS and respectively subjected to UVA radiation using a UVA irradiation chamber (Opsytech, Germany), until the desired irradiation dose was reached. At the end of the irradiation, PBS was eliminated and the cells were incubated for a further 24 hrs in RPMI with 2.5% FBS at 37° C. and 5% $CO_2$.

At the end of 24 hrs, the cell viability of the various samples was assessed according to the MTT Assay method (described above).

The data were expressed as cell viability percentage with respect to non-stressed control cells (ctr), according to the following formula:

% cell viability/ctr=(Abs sample/Abs ctr)*100

All analyses were performed at list twice in duplicate.

Results

The second set of experiments allowed to assess the protection of the extracts in case of UVA irradiation.

As for the protection data following UVA irradiation, the results underline the synergistic effect of the extracts in the 3:1 and 5:1 M/G ratio, with a cell viability increase by +25% and +19%, respectively.

| M/G | Extract | Vs UVA % Viability | Synergy |
|---|---|---|---|
| | Moringa 150 µg/mL | 89.383 | |
| | Goji 50 µg/mL | 68.862 | |
| 3:1 | Moringa 150 µg/mL + Goji 50 µg/mL | 104.964 | +25.84 |
| | Moringa 250 µg/mL | 74.504 | |
| | Goji 50 µg/mL | 77.167 | |
| 5:1 | Moringa 250 µg/mL + Goji 50 µg/mL | 94.903 | +19.07 |

BIBLIOGRAPHIC REFERENCES

Enrica Flori, Arianna Mastrofrancesco, Daniela Kovacs, Barbara Bellei, Stefania Briganti, Vittoria Maresca, Giorgia Cardinali, and Mauro Picardo, "The activation of PPARγ by 2,4,6-Octatrienoic acid protects human keratinocytes from UVR-induced damages," Scientific Reports, vol. 7, no. 1, 2017.

The invention claimed is:

1. A method for treating and/or preventing skin damages caused by ultraviolet radiation exposure in a subject, said method comprising:
    administering or topically applying to said subject a composition comprising a *Lycium barbarum* extract or *Lycium barbarum* polysaccharide in combination with a *Moringa oleifera* extract and a pharmaceutically acceptable carrier, wherein the *Moringa oleifera* extract is in a ratio of between 1:3 to 3:1, with respect to the *Lycium barbarum* extract or *Lycium barbarum* polysaccharide.

2. The method according to claim 1, wherein said skin damages are selected from actinic damage, chronic actinic damage, precancerous skin lesions, non-melanoma skin cancer.

3. The method according to claim 1, wherein the ultraviolet radiation contains UV-A, UV-B, UV-C and originates from the sun's rays.

4. The method according to claim 1, wherein the *Lycium barbarum* extract is obtained by extraction from its fruits, and the *Moringa oleifera* extract is obtained by extraction from its leaves.

5. The method according to claim 1, wherein the composition is in a form for oral administration or for topical application.

6. The method according to claim 5, wherein the composition is in a form for oral administration, and comprises further ingredients selected from vitamins, minerals, micronutrients, and mixtures thereof.

7. The method according to claim 5, wherein the composition is in a form for topical application, and further comprises adjuvant ingredients selected from cosmetic active substances and excipients.

8. A method for preventing or improving an aesthetic skin damage or skin aging caused by ultraviolet radiation exposure in a subject, wherein said method comprises: administering or topically applying to said subject a composition comprising a *Lycium barbarum* extract or *Lycium barbarum* polysaccharide in combination with a *Moringa oleifera* extract and a cosmetically acceptable carrier, wherein the *Moringa oleifera* extract is in a ratio of between 1:3 to 3:1, with respect to the *Lycium barbarum* extract or *Lycium barbarum* polysaccharide.

9. The method according to claim 8, wherein the aesthetic damage comprises one or more of skin corrugations, skin roughness, skin thickening, skin dehydration, skin wrinkling, and photoaging.

10. The method according to claim 8 wherein the composition is in a form for topical application or for oral administration.

11. The method according to claim 8 wherein said composition is in a form for oral administration, and further comprises ingredients selected from vitamins, minerals, micronutrients, and mixtures thereof.

12. The method according to claim 8, wherein said composition is in a form for topical application, and further comprises adjuvant ingredients selected from active substances and excipients used in the cosmetic field, or mixtures thereof.

13. A cosmetic method for the treatment or prevention of photoaging in a subject, said method comprising: administering or topically applying to said subject a composition comprising a *Lycium barbarum* extract or *Lycium barbarum* polysaccharide in combination with a *Moringa oleifera* extract and a physiologically acceptable carrier, wherein the *Moringa oleifera* extract is in a ratio of between 1:3 to 3:1, with respect to the *Lycium barbarum* extract or *Lycium barbarum* polysaccharide.

* * * * *